(12) United States Patent
Simon-Lopez

(10) Patent No.: US 7,256,048 B2
(45) Date of Patent: Aug. 14, 2007

(54) METHOD FOR DETECTION OF MALARIA AND OTHER PARASITE INFECTIONS

(75) Inventor: Ramon Simon-Lopez, St. Cergue (CH)

(73) Assignee: Beckman Coulter, Inc., Fullerton, CA (US)

( * ) Notice: Subject to any disclaimer, the term of this patent is extended or adjusted under 35 U.S.C. 154(b) by 386 days.

(21) Appl. No.: 11/060,957

(22) Filed: Feb. 18, 2005

(65) Prior Publication Data

US 2005/0221396 A1   Oct. 6, 2005

Related U.S. Application Data

(60) Provisional application No. 60/548,525, filed on Feb. 27, 2004.

(51) Int. Cl.
*G01N 33/48* (2006.01)
*C12Q 1/02* (2006.01)

(52) U.S. Cl. .............. 436/63; 436/8; 436/10; 436/17; 436/149; 436/150; 436/164; 435/2; 435/4; 435/29; 435/34

(58) Field of Classification Search .............. 436/8, 436/10, 17, 63, 149, 150, 164, 166, 174, 436/175; 435/2, 4, 29, 34
See application file for complete search history.

(56) References Cited

U.S. PATENT DOCUMENTS

2004/0067575 A1   4/2004   Hanaoka et al.

OTHER PUBLICATIONS

Scott, et al., "Automated detection of malaria-associated intraleucocytic haemozoin by Cell-Dyn CD4000 depolarization analysis", Clin. Lab. Haem. 25, 77-86 (2003).
Mendelow, et al., "Automated malaria detection by depolarization of laser light", British Journal of Haematology, 104, 499-503 (1999).
Kramer, et al., "Relative Frequency of Malaria Pigment-Carrying Monocytes of Nonimmune and Semi-Immune Patients from Flow Cytometric Depolarized Side Scatter", Cytometry 45, 133-140 (2001).
Grobusch, et al., "Sensitivity of Hemozoin Detection by Automated Flow Cytometry in Non- and Semi-Immune Malaria Patients", Cytometry Part B (Clinical Cytometry) 55B, 46-51 (2003).
Fourcade, et al., "Automated detection of malaria by means of the haematology analyser Coulter GEN'S", Clin. Lab. Haem. 26, 367-372 (2004).
Humar, et al., "Fatal falciparum malaria in Canadian travellers", Can. Med. Assoc. J., 156(8), 1165-1167 (Apr. 15, 1997).
Arese, et al., "Malarial pigment (haemozoin): a very active "inert" substance", Annals of Tropical Medicine and Parasitology, vol. 91, No. 5, 501-516 (1997).
Hanscheid, et al., "Avoiding misdiagnosis of malaria: a novel automated method allows specific diagnosis, even in the absence of clinical suspicion", Emerging Infectious Diseases, vol. 5, No. 6, 836-838 (Nov.-Dec. 1999).
Hanscheid, et al., "Automated Malaria Diagnosis Using Pigment Detection", Parasitology Today, vol. 16, No. 12, 549-551 (2000).
Hanscheid, et al., "Automated Detection of Malaria Pigment in White Blood Cells for the Diagnosis of Malaria in Portugal", Am. J. Trop. Med. Hyg., 64(5, 6), 290-292 (2001).
Amodu, et al., "Intraleucocyte Malaria Pigment in Asymptomatic and Uncomplicated Malaria", East African Medical Journal, vol. 74, No. 11, 714-716 (Nov. 1997).
Amodu, et al., "Intraleucocytic malaria pigment and clinical severity of malaria in children", Transactions of the Royal Society of Tropical Medicine and Hygiene, 92, 54-56 (1998).
Kueh, et al., "Haematological Alterations in Acute Malaria", Scand J Haematol, 29, 147-152 (1982).
Kain, et al., "Imported Malaria: Prospective Analysis of Problems in Diagnosis and Management", Clinical Infectious Diseases, 27, 142-149 (1998).
Eriksson, et al., "Changes in erythrocyte sedimentation rate, C-reactive protein and hematological parameters in patients with acute malaria", Scand J Infect Dis., 21(4), 434-441 (1989).
Lathia, et al., "Can Hematological Parameters Discriminate Malaria from Nonmalarious Acute Febrile Illness in the Tropics?", Indian J Med Sci, vol. 58, No. 6, 239-244 (2004).
Bunyaratvej, et al., "Cytometric Analysis of Blood Cells From Malaria-Infected Patients and in Vitro Infected Blood", Cytometry, 14:81-85 (1993).

*Primary Examiner*—Maureen M. Wallenhorst
(74) *Attorney, Agent, or Firm*—Cuspa Technology Law Associates; Mitchell E. Alter

(57) ABSTRACT

A method of detecting parasite infection, particularly malaria, includes mixing a blood sample with a lytic reagent system to lyse red blood cells, and to form a sample mixture; performing a differential analysis of white blood cells of the sample mixture on a blood analyzer, and obtaining a cell volume distribution of a white blood cell subpopulation from a cell volume measurement used in the differential analysis; obtaining a cell volume parameter from the cell volume distribution of the white blood cell subpopulation; evaluating the cell volume parameter against a predetermined criterion, and reporting an indication of the parasite infection if the cell volume parameter meets the predetermined criterion. The method also uses a discriminant obtained from cell volume parameters of two different white blood cell subpopulations against a predetermined criterion. The method further use a cell distribution parameter of a cell distribution obtained using a RF impedance measurement.

26 Claims, 2 Drawing Sheets

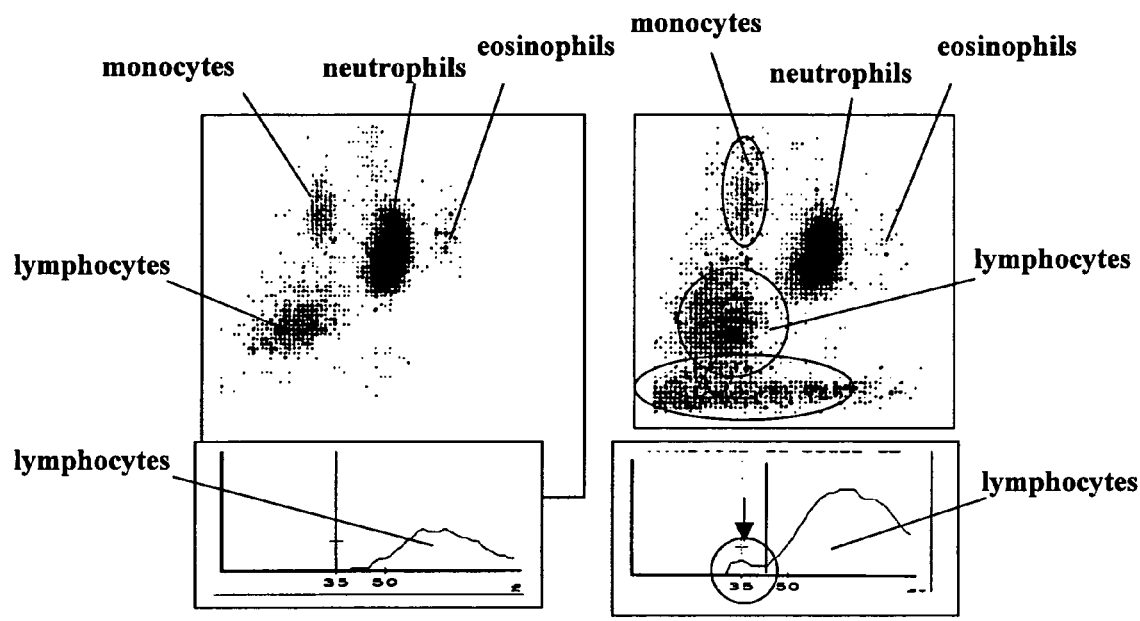

METHOD FOR DETECTION OF MALARIA AND OTHER PARASITE INFECTIONS

CROSS REFERENCE TO RELATED APPLICATION

This application claims the benefit under 35 USC 119 (e) of the provisional patent application Ser. No. 60/548,525, filed on Feb. 27, 2004, which is herein incorporated by reference in its entirety.

FIELD OF THE INVENTION

The present invention relates to a method for detection of parasite infections, particularly malaria, by measuring alteration of white blood cells of a blood sample. More specifically, it is related to a method of detection of a parasite infection based on specific alterations of cell volume and other cell properties of white blood cell subpopulations.

BACKGROUND OF THE INVENTION

Malaria remains one of the most common diseases in the world, with about 300 to 500 million cases of malaria infection estimated to occur annually. Approximately 1.5 to 2.7 million patients die annually from malaria, among them one million children are less than 5 year old. This disease, the incidence of which has been increasing for last 5 years, is today a major impediment to social and economical development in many countries. In France, 3400 cases of malaria are detected yearly, with 80% of them due to *Plasmodium falciparum*.

The pathogen agent of malaria is a protozoic parasite (*Plasmodium*) transmitted by the anopheles female to man, who is the intermediary host of the parasite. There are four types of plasmodium specific pathogen for human; *Plasmodium falciparum*, most frequently encountered in Africa, is occasionally fatal; *Plasmodium vivax*, *Plasmodium malariae* and *Plasmodium ovale* are not fatal, but may result in relapses.

The laboratory diagnosis of malaria is usually established by standard procedures that include thin and thick film examinations, based on the observation of intraerythrocytic parasites in the blood smear, and possible investigation for soluble specific antigens. However, these investigations are only undertaken if there is a clinical suspicion that a patient may actually have malaria. Although a high level of suspicion may exist in endemic areas for malaria, this is not always the case in nonendemic regions, particularly if there is a failure to take an adequate patient history. Even when there is a clinical suspicion, it is not uncommon for laboratories in nonendemic areas to have relatively poor expertise for detecting and identifying malaria. It has been reported that although a blood count is almost always requested as part of the routine investigation of febrile patients, changes in leukocyte and platelet parameters are rarely sufficiently distinctive to suggest directly a diagnosis of malaria (Kueh et al, 1982, *Scandinavian Journal of Haematology* 29, 147-152 and Eriksson et al, 1989, *Journal of Infectious Diseases* 21, 434-441). The clinical implications of these limitations are illustrated by a Canadian study (Kain et al., 1998, *Clinics in Infectious Diseases* 27, 142-149) that reported an initially missed diagnosis in 59% of returning travelers with malaria. The consequent average delay before correct diagnosis and initiation of appropriate therapy was 7.6 days for *Plasmodium falciparum* and 5.1 days for *P. vivax*. Such delays can be an important contributory factor to the development of severe malarial complications and mortality rates (Humar et al., 1997, *Canadian Medical association Journal* 156, 1165-1167).

Malaria was shown to result in leukocyte alterations, reflected mainly by the presence of hemazoin-containing pigments, produced by the various *plasmodium* species and eventually phagocytosed by neutrophils (Amodu, et al., 1997, *East African Medical Journal* 74, 714-716) and monocytes (Amodu, et al., 1997, *East African Medical Journal* 74, 714-716; Amodu, et al. 1998, *Transactions of the Royal Society of Tropical Medicine and Hygiene* 92, 54-56; Arese et al, 1997, *Annals of Tropical and Medical Parasitology* 91, 510-516). These changes were recently analyzed for providing an automated diagnosis of malaria, either by means of a flow cytometer (Krämer, et al., 2001, Cytometry 45, 133-140), or of a haematology analyzer measuring light depolarization at two wavelengths (Hänscheid, et al., 1999, *Emerging Infectious Diseases* 5, 836-838; Mendelow, et al., 1999, *British Journal of Haematology* 104, 499-503; Hänscheid, et al, 2000, *Parasitology Today* 16, 549-551; Hänscheid, et al., 2001, *American Journal of Tropical Medicine* 64, 190-192; Grobusch, et al., 2003, *Cytometry part B (clinical cytometry)* 55B, 46-51; Scott, et al., 2003, *Clinical and Laboratory Haematology* 25, 77-86).

It is desirable to be able to detect malaria on an existing hematology analyzer during a blood analysis regularly performed on the instrument, which can assist an earlier detection of the disease without additional cost. Any improved diagnosis and earlier detection can lead to a significant reduction in patient morbidity and mortality.

SUMMARY OF THE INVENTION

In one embodiment, the present invention is directed to a method of detecting a parasite infection using a blood sample. The method comprises the steps of: mixing the blood sample with a lytic reagent system to lyse red blood cells, and to form a sample mixture; performing a differential analysis of white blood cells of the sample mixture on a blood analyzer, and obtaining a cell volume distribution of a white blood cell subpopulation from a cell volume measurement used in the differential analysis; obtaining a cell volume parameter from the cell volume distribution of the white blood cell subpopulation; evaluating the cell volume parameter against a predetermined criterion, and reporting an indication of the parasite infection if the cell volume parameter meets the predetermined criterion.

The parasite infection can be *Plasmodium* infection, *Toxoplarma gondii* infection, *Leishmania* infection, or *Babesia* infection. The cell volume parameter is the mean cell volume, or standard deviation of variation of the cell volume distribution. The cell volume measurement can be an impedance measurement, a low angle light scatter measurement, or axial light loss measurement. The white blood cell subpopulation is monocytes, lymphocytes, or neutrophils.

In a further embodiment, the method comprises the steps of: mixing the blood sample with a lytic reagent system to lyse red blood cells, and to form a sample mixture; performing a differential analysis of white blood cells of the sample mixture on a blood analyzer; and obtaining a first cell volume distribution of a first white blood cell subpopulation and a second cell volume distribution of a second white blood cell subpopulation from a cell volume measurement used in the differential analysis; obtaining a first cell volume parameter from the first cell volume distribution of the first white blood cell subpopulation and obtaining a second cell volume parameter from the second cell volume distribution of the second white blood cell subpopulation; obtaining a discriminant as a function of the first and second cell volume parameters; and evaluating the discriminant against a predetermined criterion, and reporting an indication of the parasite infection if the discriminant meets the predetermined criterion. In a preferred embodiment, the first and second cell volume parameters are standard deviations of the first and second cell volume distributions, respectively, and the discriminant is a function of the standard deviations of the first and second cell volume distributions.

Furthermore, the methods described above can further include analyzing cell distribution patterns obtained from the differential analysis or from an additional differential analysis of the blood sample.

In another embodiment, the present invention is directed to a method of detecting a parasite infection using a blood sample comprising the steps of: mixing the blood sample with a lytic reagent system to lyse red blood cells, and to form a sample mixture; performing a differential analysis of white blood cells of the sample mixture on a blood analyzer, and obtaining a first cell distribution of a first white blood cell subpopulation from an impedance measurement used in the differential analysis; obtaining a first cell distribution parameter from the first cell distribution of the white blood cell subpopulation; evaluating the first cell distribution parameter against a first predetermined criterion, and reporting an indication of the parasite infection if the first cell distribution parameter meets the predetermined criterion. The method can further comprise the steps of: obtaining a second cell distribution of a second white blood cell subpopulation from the impedance measurement; obtaining a second cell distribution parameter from the second cell distribution of the second white blood cell subpopulation; obtaining a discriminant as a function of the first and second cell distribution parameters; and evaluating the discriminant against a second predetermined criterion, and reporting an indication of the parasite infection if the discriminant meets the second predetermined criterion. Herein, the impedance measurement is a direct current impedance measurement, or a radio frequency impedance measurement.

BRIEF DESCRIPTION OF DRAWINGS

FIG. 1 shows the VCS scattergrams and the DC white blood cell distribution histograms of malaria negative (left) and malaria positive (right) samples.

FIG. 2 shows a table of DC (V), Opacity (C) and RLS (S) parameters provided by the Coulter Gen*S and LH 750 hematology analyzers.

DETAILED DESCRIPTION OF THE INVENTION

Figure 3:
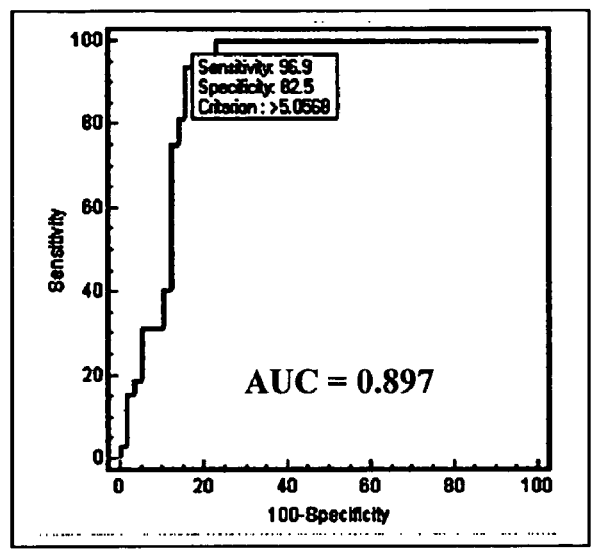
FIG. 3 shows a ROC curve of the discriminant (Vsd (lymphocytes)×Vsd (monocytes)). The cut off and the corresponding sensitivity and specificity, as well as the Area Under the Curve (AUC) are provided.

In one embodiment, the present invention provides a method for detecting a parasite infection, particularly malaria, by measuring alterations of white blood cells in a blood sample due to the disease using an automated hematology analyzer. The method comprises the steps of mixing a blood sample with a lytic reagent system to lyse red blood cells, and to form a sample mixture; performing a differential analysis of white blood cells of the sample mixture on a blood analyzer, and obtaining a cell volume distribution of a white blood cell subpopulation from a cell volume measurement used in the differential analysis; obtaining a cell volume parameter from the cell volume distribution of the white blood cell subpopulation; evaluating the cell volume parameter against a predetermined criterion, and reporting an indication of malaria if the cell volume parameter meets the predetermined criterion. As described in detail hereinafter, the cell volume can be measured using a direct current impedance measurement, low angle light scatter measurement or axial light loss measurement.

In another embodiment, upon lysing the red blood cells, and performing a differential analysis of white blood cells, the method includes the steps of obtaining a cell distribution of a white blood cell subpopulation from an impedance measurement used in the differential analysis; obtaining a cell distribution parameter from the cell distribution of the white blood cell subpopulation; evaluating the cell distribution parameter against a predetermined criterion, and reporting an indication of malaria if the cell distribution parameter meets the predetermined criterion. Herein, the impedance measurement can be a direct current impedance measurement, or a radio frequency impedance measurement. The direct current impedance measurement reflects cell volume of a cell, and the radio frequency impedance measurement reflects the intracellular contents of the cell.

The term of cell volume parameter used herein refers to a parameter related to the cell volume distribution, such as the mean of cell volume or standard deviation from the cell volume distribution of a white blood cell subpopulation. The term of cell distribution parameter used herein refers to a parameter related to the cell distribution obtained from an impedance measurement, such as the mean, or standard deviation of the cell distribution of a white blood cell subpopulation as measured by either a direct current impedance measurement, or a radio frequency impedance measurement. It is noted that the cell distributions from these two impedance measurements represent different cell properties. The term of predetermined criterion used herein refers to a criterion made based on one or more of cell volume parameters, a function of cell volume parameters, such as a threshold or cut-off value of a parameter, or a function. The predetermined criterion further includes a characteristic cell distribution pattern. In general, the criterion is determined based on differences between a plurality of normal blood samples and a specific type of abnormal blood samples, such as malaria patient samples, which are illustrated in detail hereinafter.

In a preferred embodiment, the lytic reagent system comprises a lytic reagent and a stabilizing reagent. The lytic reagent is mixed with a blood sample to lyse red blood cells, and the stabilizing reagent is added subsequently to inhibit further lytic action on white blood cells in the sample mixture. Suitable examples of lytic reagents and the stabilizing reagents and the method of use have been described in U.S. Pat. Nos. 5,155,044, 5,731,206, 5,786,224, 5,686,308 and 5,843,608, which are herein incorporated by reference in their entireties. Using these lytic reagents and the stabilizing reagents, and the method of preparing a blood sample, the white blood cells are preserved in a near native state during the measurement, and their cellular membranes are not lysed. As described in the above-referenced patents, the lysing reaction, calculated from the time that the blood sample is in contact with the lytic reagent to the time starting measurement of the sample mixture, is in a range from about 8 to about 20 seconds. The reaction and measurement of the sample mixture are at a regular room temperature ranging from about 18° C. to about 28° C.

It should be understood that other lytic reagents suitable to preserve white blood cells during the measurement of the sample mixtures can also be used for the purpose of the present invention.

In one embodiment, the differential analysis of white blood cells in the sample mixture is performed using the VCS measurement, which is utilized on various commercial hematology analyzers manufactured by Beckman Coulter, Inc. Fullerton, Calif. The VCS measurement refers to a multidimensional measurement of an impedance signal of direct current, referred to as DC, and an impedance signal of radio frequency, referred to as RF, and a medium angle light scatter signal, referred to as LS, generated by a cell in a conductive medium when the cell passes through a flow cell. Among these three measurements, both DC and RF measurements are impedance measurements, which detect the increase of impedance as a cell carried in a conductive medium passes through the flow cell. This technology has been fully described in U.S. Pat. No. 5,125,737, which is herein incorporated by reference in its entirety.

On the commercial hematology analyzer using the VCS measurement, a three-dimensional scattergram is produced. The three dimensions are DC as the z-axis, which is also referred to as "V" because a DC impedance signal directly correlates to the volume or size of a cell; Opacity (OP) as the y-axis, which is a function of RF and DC, and also referred to as "C" or conductivity because the RF signals further reflect cell contents of a cell; and Rotated Light Scatter (RLS) as the x-axis, which is a function of light scatter and DC, and also abbreviated as "S". The three-dimensional scattergram is usually displayed as a DC vs. RLS two dimensional scattergram, or a DC vs. OP two dimensional scattergram. In the DC vs. RLS scattergram, four major white blood cell subpopulations, i.e., lymphocytes, monocytes, neutrophils, and eosinophils, are differentiated from one another. In the DC vs. OP scattergram, three major groups of white blood cell subpopulations are differentiated from one another, i.e., lymphocytes, monocytes and a sum of neutrophils and eosinophils. The basophils can be differentiated using one or more gated scattergram. It is noted that to differentiate lymphocytes, monocytes, or neutrophils from other cell types, one can use all three measurements, i.e., DC, RF and RLS, or only two measurements, either DC and LS, or DC and RF. Furthermore, various other methods such as multi-angle light scatter measurement using forward scatter and side scatter, or low angle and medium angle light scatter can be used for differentiating white blood cell subpopulations, particularly lymphocytes, monocytes, or neutrophils from other cell types.

It has been found that the properties of white blood cells of a malaria patient are altered, particularly the volumes and the homogeneities of cell volume of specific white blood cell subpopulations are altered. More specifically, it has been found that when measured by the VCS measurement, the DC means of monocytes and neutrophils, and the standard deviations of DC and Opacity of the lymphocytes and monocytes of the malaria samples increase to the levels that the differences of these parameters from those of normal blood samples are statistically significant. Among these parameters, DC means directly relate to cell volume, and the standard deviation of a parameter reflects the homogeneity or heterogeneity of one or more cell properties represented by that parameter. The changes of these parameters of white blood cell subpopulations can be utilized as an indicator or discriminant for detection of malaria.

It should be understood that the increases of DC mean, standard deviation of DC, and Opacity of the monocytes are caused by the presence of large monocytic cells which mainly include activated monocytes, macrophages, and pigment-carrying monocytes. Similarly, the increases of the standard deviations of DC and Opacity of the lymphocytes are caused by the presence of large lymphocytes which mainly include reactive and activated lymphocytes; and the increase of the DC mean of the neutrophils is caused by the presence of large neutrophils which mainly include immature and activated neutrophils, and neutrophils phagocyting parasites. Therefore, the term of "monocytes" used herein include monocytes, activated monocytes, macrophages, pigment-carrying monocytes, and other monocytic cells such as monoblasts, promonocytes, and myeloid related dendritic cells. The term of "lymphocytes" used herein include lymphocytes, reactive and activated lymphocytes. The term of "neutrophils" used herein include neutrophils, immature and activated neutrophils, and neutrophils phacocyting parasites. The pigment-carrying white blood cells refer to the white blood cells that contain intracellular pigments produced by parasite digestion, such as hemozoin-carrying monocytes and neutrophils in a malaria patient's blood sample. The hemozoin is produced by *Plasmodium* species as an end product of hemoglobin digestion.

In one embodiment, as illustrated in the Example described hereinafter, the cell volume and its distribution of an individual white blood subpopulation are determined by the DC impedance measurement. It should be understood, however, the cell volume can also be determined by other suitable means, such as forward or low angle light scatter, or axial light loss measurement. In general, the low angle light scatter is defined as the light scatter signals measured in less than 10° from the incident light. Axial light loss (ALL, also known as forward extinction) is generally the decrease in light energy due to a particle passing through a beam of incident light and being detected by a photo-detector. Generally ALL signals are detected at an angle from about 0° to about 1° from the incident light. Both low angle light scatter and ALL signals are strongly influenced by the size of the cell. The apparatus and method of measuring low angle light scatter and ALL signals known in the art can be used for the purpose of the present invention for measurement of the cell volume.

In a further embodiment, the detection of malaria can be accomplished by combining the information of cell property change from two or more different white blood cell subpopulations, for example, combining the cell volume parameters from two different white blood cell subpopulations, or combining a cell volume parameter of one white blood cell subpopulation with a standard deviation of Opacity of another white blood cell subpopulation. It has been found that using a discriminant as a function of more than one detectable parameters can further improve sensitivity and specificity than using one parameter from only one cell type.

In one embodiment, the discriminant defined by the following equation is used as a sensitive and specific indicator of malaria:

$$D = Vsd(\text{lymphocytes}) \times Vsd(\text{monocytes})/100$$

wherein D stands for the discriminant; V stands for the cell volume determined by DC measurement; sd stands for standard deviation; Vsd stands for the standard deviation of cell volume; and Vsd (lymphocytes) stands for standard deviation of cell volume of lymphocytes obtained from the DC measurement.

As illustrated in the Example, the method of the present invention using the discriminant described above has demonstrated high sensitivity and specificity for detecting malaria, which are comparable to known methods which utilize depolarized light scatter measurement.

The method of detection of malaria using a blood sample described above can also be used for detection of other parasite infections, such as *Toxoplarma gondii* infection, *Leishmania* infection, and *Babesia* infection. Similar to *Plasmodium* infection which is the cause of malaria, there are activated monocytes and macrophages in the peripheral blood of the patients when the patient has *Toxoplarma gondii*, *Leishmania*, or *Babesia* infections. The criterion for indication of a specific parasite infection, such as the cut-off value of a cell distribution parameter, can be determined for each specific infection.

Additionally, the method can further include pattern recognitions of cell distribution characteristics which relate to the disease. For example, as shown in FIG. 1, an additional population below the lymphocytes in DC is typically observed in the malaria samples. The specific cell distribution characteristics can be utilized to further enhance the sensitivity and specificity of the detection method.

In a further embodiment, the method of the present invention utilizes two separate white blood cell measurements for detecting malaria. More specifically, the method comprises the steps of exposing a first aliquot of a blood sample to a first lytic reagent system to lyse red blood cells and to form a first sample mixture; exposing a second aliquot of the blood sample to a second lytic reagent system to lyse red blood cells and to form a second sample mixture; performing a first differential analysis of white blood cells of the first sample mixture on a blood analyzer, and obtaining a cell volume distribution of a white blood cell subpopulation; performing a second differential analysis of white blood cells of the second sample mixture by a DC impedance measurement on the blood analyzer, and obtaining a cell distribution of white blood cells using the DC impedance measurement; obtaining a cell volume parameter from the obtained cell volume distribution of the first sample mixture; analyzing patterns of the obtained cell distribution of the second sample mixture; performing a combined analysis on a profile obtained by combining results of the two analyses, the combined analysis evaluating the profile against a predetermined malaria criterion; and reporting indication of malaria of the blood sample if the profile meets the predetermined malaria criterion.

The first lytic reagent system, the first differential analysis of white blood cells of the first sample mixture and the cell volume parameters from the obtained cell volume distribution of the first sample mixture are the same as those described above using the VCS measurement.

The second lytic reagent system suitable for lysing blood sample for the purpose of the present invention can comprise an isotonic blood diluent and a lysing reagents, such as those described in U.S. Pat. Nos. 4,346,018, 4,521,518, 4,528,274, 4,962,038, 5,763,280, 5,834,315, 5,882,934, 5,935,857 and 6,573,102, which are herein incorporated by reference in their entireties. One example of the second lytic reagent system is the Lyse S® III Diff lytic reagent and Isoton® III diluent manufactured by Beckman Coulter, Inc., California. Another suitable example is Lyse S® 4 lytic reagent and Isoton® 4 diluent manufactured by the same manufacturer. Alternatively, the reagent system can also be an isotonic lysing reagent as described in U.S. Pat. No. 5,882,934, which is hereby incorporated by reference in its entirety. This reagent dilutes the blood sample and lyses the red blood cells at the same time for subsequent analysis.

The method of performing a second differential analysis of white blood cells of the second sample mixture by a DC impedance measurement on the blood analyzer, and obtaining a cell distribution of white blood cells using the DC impedance measurement have been described fully in U.S. Pat. Nos. 4,286,963, 4,485,175 and 6,673,618 B1, which are herein incorporated by reference in their entireties.

On the hematology analyzer used herein, the second aliquot of the blood sample is diluted by a blood diluent and then mixed with a predetermined amount of a second lytic reagent to lyse the red blood cells, which forms the second sample mixture. Using the lytic reagents described above, the white blood cells are partially lysed. The obtained cell distribution depends on, in a certain degree, the nuclear volumes of white blood cell subpopulations, which is different from the cell volume distribution from the measurement of the first sample mixture. Typically, from this cell distribution the white blood cells can be differentiated into two or three subpopulations, commonly referred to as a two-part differential or a three-part differential. The three-part differential differentiates the white blood cells into lymphocytes, monocytes and granulocytes. It has been found that in the malaria samples there is an additional population present on the left side of lymphocytes, as shown in FIG. 1, which may be attributed to the parasites in the red blood cells or the ingested malaria pigments in the white blood cells. Such a cell distribution characteristics can be utilized to further improve sensitivity and specificity of detection of malaria using the method described above which is based on the analysis of the first sample mixture.

Therefore, in one embodiment, the analysis of cell volume parameters of the obtained cell volume distribution of the first sample mixture as described above can be combined with the analysis of patterns of the obtained cell distribution of the second sample mixture to produce a profile. A combined analysis evaluates the profile against a predetermined malaria criterion, and reports indication of malaria of the blood sample if the profile meets the predetermined malaria criterion.

The following examples are illustrative of the invention and are in no way to be interpreted as limiting the scope of the invention, as defined in the claims. It will be understood that other variations of the methods may be employed, in accordance with the proceeding disclosure.

EXAMPLE (a) Patients 89 clinical whole blood samples for investigations for malaria were analyzed. These samples were required for hematology analysis by physicians, on the basis of unexplained fever in patients either originating from or having traveled in endemic areas. 32 of them were recognized positive for malaria, due either to *Plasmodium falciparum* (28 cases) or *Plasmodium vivax* (4 cases). 57 were found negative by the reference method described hereinafter. The age of the patients ranged from 8 month to 72 year old.

(b) Hematology Analyzer

All samples, either malaria positive or malaria negative, were run on a Coulter GEN*S™ hematology analyzer (manufactured by Beckman Coulter, Inc., California). The hematology analyzer is herein also referred to as instrument. The hematology analyzer provides two separate white blood cell differential analyses. The first differential analysis is performed using the VCS measurement of the first sample mixture prepared by mixing a first aliquot blood sample with an amount of Erythrolyse™ II to lyse red blood cells and subsequently mixing with an amount of Stabilyse™ to stabilize the white blood cells. The VCS measurement differentiates the white blood cells into five subpopulations, i.e., lymphocytes, monocytes, neutrophils, basophils and eosinophils. The second differential analysis is performed by using a DC impedance measurement of the second sample mixture prepared by diluting a second aliquot blood sample with Isoton® III diluent and mixing with an amount of Lyse S® III Diff reagent. The DC impedance measurement provides a total count of white blood cells and also differentiates the white blood cells into three subpopulations, i.e., lymphocytes, monocytes and granulocytes using an one dimensional DC histogram, which is commonly referred to as WBC histogram. For the purpose of reflecting the detection method, it is herein referred to as WBC DC histogram. All reagents described above are manufactured by Beckman Coulter, Inc., California.

FIG. 1 shows two DC vs. RLS scattergrams, one from a malaria negative patient and one from a malaria positive patient, and two WBC DC histograms. Several distribution features were observed in the malaria positive sample, including increased volume heterogeneity of the monocyte and lymphocyte populations, the presence of an additional population below the lymphocyte population, and the presence of an additional population on the left side of lymphocytes of the WBC DC histogram. These features have been frequently observed in malaria patients.

The parameters shown in FIG. 2 are accessible on an additional screen of the hematology analyzer, which include the mean values of DC or volume (shown as V), Opacity shown as (C) and Rotated Light Scatter (shown as S) for each of the four major populations, and the standard deviations (SD) of volume, Opacity and Rotated Light Scatter.

Furthermore, the hematology analyzer allows the user to create decision rules according to criteria chosen by the operator. These rules were recently shown to provide an accurate alarm system (Amouroux, et al., 2003, *règles de décision. Annales de Biologie Clinique* 61, 576-584) for detecting the blood abnormalities of the whole blood samples.

(c) Reference Method

All samples were analyzed as "malaria positive" or "malaria negative" patients by a blood smear investigation, which showed the presence or the absence of plasmodium invasion of the red blood cells (RBC). In the 32 samples of the positive group, the percentage of invaded RBC ranged from 0.1% to 4.65%.

(d) Statistical Methods

The mean values and standard deviations (SD) of DC, Opacity and Rotated Light Scatter of lymphocytes, monocytes and neutrophils were taken from the table given by the hematology analyzer (FIG. 2) for each sample. DC, Opacity and Rotated Light Scatter are referred to in the table of the instrument display as V, C, and S, respectively.

The patients were divided into two groups, malaria negative or malaria positive. The parameters were first submitted to a non-parametric test (Wilcoxon rank test), in order to compare to each other the results of the negative and of the positive groups. The parameters which were found significantly different by this test were then submitted to a Receiver Operator Characteristic Curve (ROC) analysis, to determine whether the changes observed between the two groups were malaria specific and to determine the optimal cut off criteria for detection of the malaria. A ROC analysis was also performed on discriminants derived from the DC or volume parameters of the monocytes and lymphocytes.

(e) Evaluation of the Selected Parameters

Since the DC (volume) parameters of monocytes and lymphocytes were shown by the statistical analysis more efficient for distinguishing the malaria positive from the malaria negative patients, they were further evaluated in terms of repeatability, stability of the hematology analyzer over one month, variability from one instrument to another, time dependent variation of the parameters of the samples at different sample ages.

The repeatability was investigated with ten blood samples from blood donors. Each sample was run ten times on the hematology analyzer and the coefficient of variation (CV) of the volume parameters of monocytes and lymphocytes were calculated for each sample. The repeatability for each parameter was then expressed as the average CV of the ten samples. The repeatability of Vsd (lymphocyte) and Vsd (monocyte) was calculated according to the procedure described above. The mean coefficients of variation of these values were 4.4% and 5.5% respectively.

Figure 5:
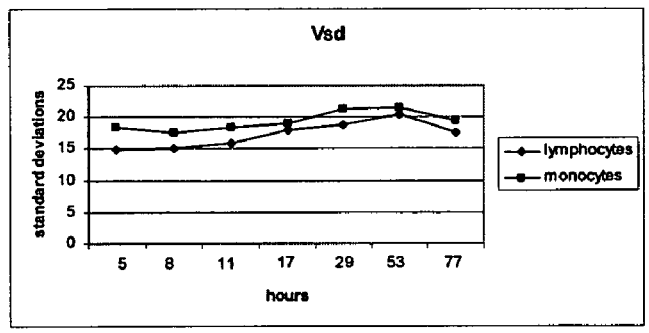
FIG. 5 shows the time dependent variation of Vsd (monocytes) and Vsd (lymphocytes) of a group of 15 blood donors.

The sample age dependent variation was evaluated as the variation of a parameter over 77 hours after the blood collection. A group of 15 samples from blood donors were collected and run on the same instrument at 5, 8, 11, 17, 29, 53 and 77 hours after the blood collection. The averages of the volumes and standard deviations of the volume of lymphocytes and monocytes were calculated, respectively, to evaluate the variations of these parameters during a period of 77 hours. As shown in FIG. 5, the Vsd (lymphocyte) and Vsd (monocyte) are stable within 11 hours after the collection of the blood samples. The mean values of Vsd (lymphocyte) and Vsd (monocyte) at 5, 8 and 11 hours after the blood collection were 14.8, 15, 15.9 and 18.3, 17.5, 18.4 respectively.

Figure 4:
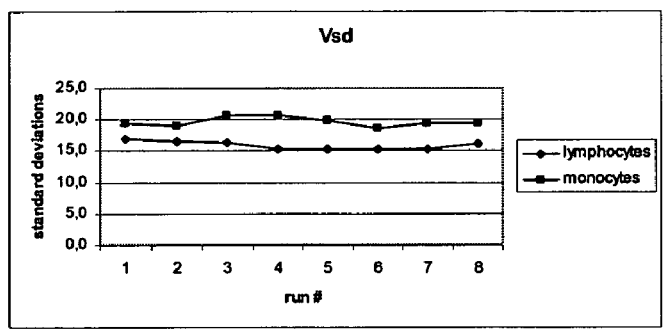
FIG. 4 shows the variation of Vsd (monocytes) and Vsd (lymphocytes) of several groups of samples from blood donors collected over one month (each group includes 10 donors).

The stability of the hematology analyzer was investigated separately on a LH750 hematology analyzer which had the same VCS detection system as that on the Gen*S, and was manufactured by the same manufacturer. The stability was investigated over one month by running periodically groups of blood samples from the donors, each group including ten samples. The average of the volumes and standard deviations of the volumes of lymphocytes and monocytes were calculated for each group, which allowed monitoring the variability of normal values in one month. The stability of the instrument is shown in FIG. 4. Over a time period of one month, the average values of Vsd (lymphocyte) and Vsd (monocyte) of the blood samples from the groups of blood donors varied in the range 18.6-20.6 (mean: 19.6) and 15.3-16.9 (mean: 15.9) respectively, with a CV equal to 4% for both values.

The comparison between instruments was performed by using two LH 750 hematology analyzers, and both were set according to the manufacturer's requirements. 85 whole blood samples from blood donors were run on the first instrument and 81 on the second instrument. The means of Vsd (lymphocyte) and Vsd (monocyte) were compared by calculating the percentage variation between the two instruments. The results of comparison between instruments are given in Table 1. As shown, the Vsd (lymphocyte) and Vsd (monocyte) reported from two different instruments are consistent. The percentage variation of Vsd (lymphocyte) and Vsd (monocyte) between these two instruments were 3.2% and 1.5%, respectively.

TABLE 1

Variation between instruments of the Vsd of lymphocytes and the Vsd of monocytes

|  | Vsd lymphocytes | Vsd monocytes |
| --- | --- | --- |
| Instrument 1 (85 donors) | | |
| Mean | 15.5 | 19.5 |
| 95% confidence interval | 15.2–15.9 | 19.3–19.8 |
| Instrument 2 (81 donors) | | |
| Mean | 16 | 19.2 |
| 95% confidence interval | 15.7–16.3 | 18.9–19.6 |
| Variation (%) | 3.2% | 1.5% |

(f) Results

A first analysis of the instrument reported DC, Opacity and RLS parameters was performed for lymphocytes, monocytes and neutrophils of the positive and negative groups. This analysis was performed using the non-parametric test (Wilcoxon rank test). Table 2 shows the statistical results of the two groups (mean and standard deviation for each parameter), as well as the significance of the differences.

From Table 2, it can be seen that significant differences were observed in one neutrophil parameter, i.e., mean volume, two lymphocyte parameters, i.e., standard deviation of volume and standard deviation of Opacity, and three monocyte parameters, i.e., mean volume, standard deviation of volume and standard deviation of Opacity. These six parameters that exhibited significant differences between the two groups were submitted to a ROC analysis. Table 3 shows the results of the ROC analysis for each of the parameters investigated, in terms of sensitivity, specificity and cut off values. The area under the ROC curve (AUC) is also given.

Furthermore, a discriminant (D) defined by the formula shown below was derived from these two parameters to further improve the specificity of the detection:

$$D = Vsd(\text{lymphocytes}) \times Vsd(\text{monocytes})/100$$

TABLE 2

Parameters exhibiting a significant difference between the malaria positive and the malaria negative groups.

|  | Vmean | Cmean | Smean | Vsd | Csd | Ssd |
|---|---|---|---|---|---|---|
| Neutrophils |  |  |  |  |  |  |
| Positive | 151.8 ± 11.9 | 132.4 ± 5.3 | 142.9 ± 6.6 | 22.6 ± 3.5 | 8.0 ± 2.1 | 12.0 ± 2.3 |
| Negative | 145.7 ± 12.4 | 134.6 ± 4.7 | 140.9 ± 11.6 | 21.4 ± 4.3 | 7.3 ± 1.4 | 11.9 ± 2.5 |
| Significance | p = 0.0059 | NS | NS | NS | NS | NS |
| Lymphocytes |  |  |  |  |  |  |
| Positive | 85.3 ± 10.6 | 103.0 ± 3.1 | 67.1 ± 8.4 | 27.6 ± 4.2 | 16.1 ± 2.8 | 17.6 ± 2.3 |
| Negative | 82.6 ± 6.9 | 102.9 ± 4.6 | 66.5 ± 6.1 | 20.3 ± 4.4 | 13.0 ± 2.4 | 18.3 ± 1.7 |
| Significance | NS | NS | NS | p = 0.0000 | p = 0.0000 | NS |
| Monocytes |  |  |  |  |  |  |
| Positive | 186.6 ± 12.1 | 111.3 ± 4.6 | 88.6 ± 3.9 | 24.7 ± 3.6 | 5.0 ± 0.9 | 9.3 ± 1.1 |
| Negative | 170.4 ± 11.9 | 111.7 ± 3.2 | 87.7 ± 4.6 | 20.1 ± 4.1 | 4.8 ± 0.4 | 9.6 ± 1.4 |
| Significance | p = 0.0000 | NS | NS | p = 0.0000 | p = 0.0152 | NS |

As shown, the cut-off values obtained from the ROC analysis are used as the criterion for indication of malaria. The results described in Table 3 showed that two parameters (Vsd (lymphocytes) and Vsd (monocytes)) exhibited sensitivity higher than 90% and specificity higher than 60%, with AUC of 0.876 and 0.822, respectively. Thus, these two parameters are particularly favorable for distinguishing the malaria positive from the malaria negative samples.

As shown in FIG. 3, the ROC analysis performed on this discriminant showed that a discriminant value higher than 5.06 indicated the presence of malaria with a sensitivity of 96.9% and specificity of 82.5%. Moreover, the cut off value corresponding to 100% sensitivity was 4.81, with a specificity of 77.2%.

Therefore, this discriminant significantly improved the specificity to 82.5% with a high sensitivity of 96.8%. As shown in Table 4, the performance of using this discriminant for detecting malaria is comparable with those known detection methods reported in the literature.

TABLE 3

ROC analysis of the six parameters significantly different in the malaria positive and the malaria negative groups.

|  | Vmean neutrophils | Vmean monocytes | Vsd lymphocytes | Vsd monocytes | Csd lymphocytes | Csd monocytes |
|---|---|---|---|---|---|---|
| Cut off | 141.5 | 181.6 | 22.9 | 19.9 | 14.4 | 4.9 |
| Sensitivity (%) | 84.4 | 68.7 | 90.6 | 96.9 | 81.3 | 68.7 |
| Specificity (%) | 50.0 | 85.3 | 75.4 | 63.2 | 77.2 | 71.4 |
| AUC | 0.677 | 0.844 | 0.876 | 0.822 | 0.791 | 0.656 |

TABLE 4

Comparison of the performance of the D discriminant as a test for detecting the malaria positive patients with references.

| Reference* | Detection Method/Instrument | Sensitivity | Specificity |
|---|---|---|---|
| Scott, et al. (2003) | Depolarization analysis (Abbott CD4000) | 80.2% | 87.3% |
| Grobusch, et al. (2003) | Depolarization analysis (Abbott CD3000) | 48.6% | 96.2% |
| Krämer, et al. (2001) | Depolarized side scatter - one wavelength (Cytomation Mo Flow) | 92% | 100% |
| Krämer, et al. (2001) | Correlated side scatter - two wavelengths (Cytomation MoFlow) | 95% | 94% |
| Hänchcid, et al. (2001) | Depolarization analysis (Abbott CD3500) | 95% | 88% |

TABLE 4-continued

Comparison of the performance of the D discriminant as a test for detecting the malaria positive patients with references.

| Reference* | Detection Method/Instrument | Sensitivity | Specificity |
|---|---|---|---|
| Mendelow, et al. (1999) | Depolarization analysis (Abbott CD3500) | 72% | 96% |
| The method of the instant invention | Analysis of volume parameters (Beckman Coulter GEN*S) | 96.8% | 82.5% |

*Scott, et al., 2003, Clinical and Laboratory Haematology 25, 77–86
Grobusch, et al., 2003, Cytometry part B (clinical cytometry) 55B, 46–51
Krämer, et al., 2001, Cytometry 45, 133–140
Hänscheid, et al., 2001, American Journal of Tropical Medicine 64, 190–192
Mendelow, et al., 1999, British Journal of Haematology 104, 499–503

The invention has been described with reference to particularly preferred embodiments. It will be appreciated, however, that various changes can be made without departing from the spirit of the invention, and such changes are intended to fall within the scope of the appended claims. While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A method of detecting a parasite infection using a blood sample comprising the steps of:
    (a) mixing said blood sample with a lytic reagent system to lyse red blood cells, and to form a sample mixture;
    (b) performing a differential analysis of white blood cells of said sample mixture on a blood analyzer, and obtaining a cell volume distribution of a white blood cell subpopulation from a cell volume measurement used in said differential analysis;
    (c) obtaining a cell volume parameter from said cell volume distribution of said white blood cell subpopulation;
    (d) evaluating said cell volume parameter against a predetermined criterion, and reporting an indication of said parasite infection if said cell volume parameter meets said predetermined criterion.

2. The method of claim 1, wherein said white blood cell subpopulation is monocytes.

3. The method of claim 1, wherein said white blood cell subpopulation is lymphocytes.

4. The method of claim 1, wherein said white blood cell subpopulation is neutrophils.

5. The method of claim 1, wherein said cell volume parameter is a standard deviation of said cell volume distribution.

6. The method of claim 1, wherein said cell volume parameter is a mean of said cell volume distribution.

7. The method of claim 1, wherein said cell volume measurement is an impedance measurement.

8. The method of claim 1, wherein said cell volume measurement is a low angle light scatter measurement, or an axial light loss measurement.

9. The method of claim 1, wherein said parasite infection is *Plasmodium* infection.

10. The method of claim 1, wherein said parasite infection is *Toxoplarma gondii* infection, *Leishmania* infection, or *Babesia* infection.

11. A method of detecting a parasite infection using a blood sample comprising the steps of:
    (a) mixing said blood sample with a lytic reagent system to lyse red blood cells, and to form a sample mixture;
    (b) performing a differential analysis of white blood cells of said sample mixture on a blood analyzer; and obtaining a first cell volume distribution of a first white blood cell subpopulation and a second cell volume distribution of a second white blood cell subpopulation from a cell volume measurement used in said differential analysis;
    (c) obtaining a first cell volume parameter from said first cell volume distribution of said first white blood cell subpopulation and obtaining a second cell volume parameter from said second cell volume distribution of said second white blood cell subpopulation;
    (d) obtaining a discriminant as a function of said first and second cell volume parameters; and
    (e) evaluating said discriminant against a predetermined criterion, and reporting an indication of said parasite infection if said discriminant meets said predetermined criterion.

12. The method of claim 11, wherein said first and second cell volume parameters are standard deviations of said first and second cell volume distributions, respectively; and said discriminant is a function of said standard deviations of said first and second cell volume distributions.

13. The method of claim 11, wherein said first white blood cell subpopulation is monocytes.

14. The method of claim 11, wherein said second white blood cell subpopulation is lymphocytes.

15. The method of claim 11, wherein said cell volume measurement is an impedance measurement.

16. The method of claim 11, wherein said cell volume measurement is a low angle light scatter measurement, or an axial light loss measurement.

17. The method of claim 11, wherein said parasite infection is *Plasmodium* infection.

18. The method of claim 11, wherein said parasite infection is *Toxoplarma gondii* infection, *Leishmania* infection, or *Babesia* infection.

19. A method of detecting a parasite infection using a blood sample comprising the steps of:
    (a) mixing said blood sample with a lytic reagent system to lyse red blood cells, and to form a sample mixture;

(b) performing a differential analysis of white blood cells of said sample mixture on a blood analyzer, and obtaining a first cell distribution of a first white blood cell subpopulation from an impedance measurement used in said differential analysis;

(c) obtaining a first cell distribution parameter from said first cell distribution of said white blood cell subpopulation;

(d) evaluating said first cell distribution parameter against a first predetermined criterion, and reporting an indication of said parasite infection if said first cell distribution parameter meets said predetermined criterion.

20. The method of claim 19, wherein said impedance measurement is a direct current impedance measurement, or a radio frequency impedance measurement.

21. The method of claim 19, wherein said cell distribution parameter is a standard deviation of said first cell distribution.

22. The method of claim 19, wherein said cell distribution parameter is a mean of said first cell distribution.

23. The method of claim 19, wherein said parasite infection is *Plasmodium* infection.

24. The method of claim 19, wherein said parasite infection is *Toxoplarma gondii* infection, *Leishmania* infection, or *Babesia* infection.

25. The method of claim 19, wherein said white blood cell subpopulation is monocytes, lymphocytes, or neutrophils.

26. The method of claim 19 further comprising the steps of:

obtaining a second cell distribution of a second white blood cell subpopulation from said impedance measurement;

obtaining a second cell distribution parameter from said second cell distribution of said second white blood cell subpopulation;

obtaining a discriminant as a function of said first and second cell distribution parameters; and evaluating said discriminant against a second predetermined criterion, and reporting an indication of said parasite infection if said discriminant meets said second predetermined criterion.

* * * * *